United States Patent
Howard et al.

(10) Patent No.: US 6,207,176 B1
(45) Date of Patent: Mar. 27, 2001

(54) STARCH BASED ADHESIVES FOR SKIN CLEANING TAPE

(75) Inventors: Doreen L. Howard, Plainsboro; Frank A. Nowak, Jr., Somerville; Daniel B. Solarek, Belle Mead; James L. Eden, E. Millstone; Gary T. Martino, Jamesburg, all of NJ (US)

(73) Assignee: National Starch and Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/152,828

(22) Filed: Sep. 14, 1998

(51) Int. Cl.⁷ .............................. A01N 25/34; A61K 6/00; A61K 7/00; A61K 31/74; C09J 5/02
(52) U.S. Cl. .................. 424/402; 424/78.02; 424/78.03; 424/401; 424/447; 424/448; 424/449; 514/844; 514/846; 156/326; 536/45; 536/102; 536/105
(58) Field of Search .................................. 424/402, 70.1, 424/78.03, 78.02, 447, 448, 449, 401; 514/844, 846; 156/326; 536/45, 102, 105

(56) References Cited

U.S. PATENT DOCUMENTS 5,512,277 * 4/1996 Uemura et al. ................... 424/78.03
5,968,537 * 10/1999 Crotty et al. ......................... 424/402

* cited by examiner

Primary Examiner—Thurman K. Page
Assistant Examiner—Todd D Ware
(74) Attorney, Agent, or Firm—Karen G. Kaiser, Esq.; Thomas F. Roland, Esq.

(57) ABSTRACT

This invention involves skin cleaning products and tapes for removing keratotic plugs, dirt and other debris found on the skin and in skin pores and comprising a starch based remoistenable adhesive composition wherein the starch has from about 0 to 70% by weight amylose content and is converted to from about 30 WF to 20 DE.

25 Claims, No Drawings

STARCH BASED ADHESIVES FOR SKIN CLEANING TAPE

BACKGROUND OF THE INVENTION

This invention relates to the use of selected starch based adhesives in skin cleaning tapes to remove keratotic plugs as well as dirt and other matter from skin and skin pores.

Keratotic plugs are dead epidermal cells and oil which together with sebum, dirt and other skin debris can block and plug the pores of the skin. The formation of such plugs and skin build up are often conspicuous and can provide undesirable cosmetic effects. Additionally, if proper treatment is not given and these plugs and other build ups are not removed, various skin problems can arise.

Since keratotic plugs are formed deep in the skin, the use of traditional cleansers and detergents like soap, make-up removers and face masks are usually not effective in their removal. There has not been much disclosure of skin cleaning compositions or methods to alleviate this problem. One method shown to remove keratotic plugs is found in U.S. Pat. No. 5,512,277 issued on Apr. 30, 1996 to T, Uemura et al, which discloses the use of synthetic cationic polymer compositions containing salt forming groups.

There is the need for additional skin cleaning and keratotic plug removing products particularly one which is based on the use of natural readily available materials.

SUMMARY OF THE INVENTION

This invention relates to skin cleaning tapes for removing keratotic plugs and other debris and dirt found on the skin and in skin pores and comprising a remoistenable starch based adhesive composition applied to a substrate backing material. More particularly, this invention involves skin cleaning products comprising a starch based remoistenable adhesive composition wherein the starch has from about 0 to 70% by weight of amylose content and is converted to from about 30 WF (water fluidity) to 20 DE (dextrose equivalents).

This invention further involves a method for removing keratotic plugs from the skin using the selected remoistenable starch based adhesive as described herein.

DETAILED DESCRIPTION OF THE INVENTION

The present invention provides water-soluble, remoistenable, starch based adhesives for use as keratotic plug removers. The water soluble adhesives are coated or otherwise formed on a backing substrate which is then used to apply the adhesive composition to the skin to be treated.

The adhesive polymer used in this invention has good film forming properties, is easily remoistenable or re-wettable and provides good adhesion to the skin. More particularly, the adhesive polymer is a starch material which has an amylose content of from about 0 to 70% by weight, preferably from about 0 to 55% by weight and more preferably from about 0 to 30% by weight. This starch material is converted or degraded by techniques such as acid hydrolysis, oxidation or enzyme conversion to a level of conversion of from about 30 WF (water fluidity) to 20 DE (dextrose equivalents) and more particularly from about 70 WF to 10 DE.

The base material used as the adhesive or polymer material in this invention is a starch and may be derived from any plant source including corn, potato, wheat, rice, tapioca, sago, sorghum, waxy maize and high amylose starch such as high amylose corn having up to 70% and preferably up to 55% by weight of amylose content. More particularly, the starch material will have an amylose content of from about 0 to 55% and preferably from about 0 to 30% by weight.

The starch material used in this invention is converted to from about 30 WF (water fluidity) to 20 DE (dextrose equivalents) and preferably from about 40 WF to 10 DE. Water fluidity and dextrose equivalents are measures which indicate the degree of conversion or degradation of starch. Water fluidity (WF) is an inverse viscosity measurement with higher numbers representing a more degraded starch with thinner viscosity. One way to measure WF is by use of a Thomas Rotational Shear Type Viscometer (manufactured by Arthur H. Thomas Co., Philadelphia, Pa.) in accordance with standard procedures as disclosed in U.S. Pat. No. 4,499,116 issued Feb. 12, 1985 to Zwiercan et al. Dextrose equivalent is also a measure of starch conversion and is an indication of the total reducing value of starch or converted starch calculated as dextrose and expressed as a percentage of total dry substance. One known method of determining dextrose equivalents is the Fehling Volumetric method as adapted from the Exyon-Lane Volumetric Method #423 of the Cane Sugar Handbook by Spencer and Mead (John Wiley and Son Inc.).

The conversion of starch for use in this invention may be accomplished by known techniques such as acid hydrolysis, oxidation or enzyme conversion. Acid hydrolysis typically involves treatment of heated granular starch with mineral acid such as hydrochloric or sulfuric acid. Oxidation involves treatment of starch with an oxidizing agent such as sodium hypochlorite or using hydrogen peroxide and a catalytic amount of manganese salt as disclosed in U.S. Pat. No. 4,838,944 issued Jun. 13, 1989 to L. Kruger. Enzyme conversion involves treatment of granular starch slurried in water using an enzyme, e.g., alpha amylase enzyme at pH of about 5.6 to 5.7. A recently disclosed method involving enzyme conversion is the single phase, high solids enzyme conversion process described in U.S. Pat. No. 5,688,845 issued Nov. 18, 1997 to J. Eden et al, U.S. Pat. No. 5,795,395 issued Aug. 18, 1998 to Y. Shi et al and pending application Ser. No. 08/643,719 filed May 6, 1996 to Y. Shi et al. A further description of known starch conversion processes may be found in "Converted Starches" by O. B. Wurzburg, *Modified Starches*, Chapter 2, pp. 17–40, 1986.

The single phase, high solids enzyme conversion process described in the '845 and '395 patents and the pending Ser. No. 643,719 application referred to above comprises the steps of:

(a) adding, to a modified or unmodified, pregelatinized or ungelatinized starch, water and a starch-hydrolyzing enzyme in an amount sufficient to produce a single phase powdered mixture without a visible free water phase;

(b) activating the enzyme by heating the powdered mixture to about the optimum temperature for the enzyme while maintaining a substantially constant moisture content (i.e., within ±5% from the starting moisture content) in the mixture;

(c) allowing the enzyme to hydrolyze the starch; and (d) optionally inactivating the enzyme.

Suitable enzymes for use herein include bacterial, fungal, plant and animal enzymes such as endo-alpha-amylases which cleave the 1→4 glucosidic linkages of starch, beta-amylases which remove maltose units in a stepwise fashion from the non-reducing ends of the alpha-1→4 linkages, glucoamylases which remove glucose units in a stepwise manner from the non-reducing end of starch molecules and cleave both the 1→4 and 1→6 linkages, and debranching enzymes such as isoamylase and pullulanese which cleave the 1→6 glucosidic linkages of amylopectin-containing starches. Alpha-amylases or mixtures thereof with other enzymes are preferred and are used for preparing the enzyme-converted maltodextrins with defined bimodal or polymodal molecular weight profiles as described herein.

Process conditions for the use of a particular enzyme in the single phase enzyme conversion process will vary and will usually be suggested by the supplier. The variables include temperature, pH, substrate solids concentration, enzyme dose, reaction time and the presence of activators. Very often there are no absolute optimum reaction conditions. The "optimum" pH may depend on temperature; the "optimum" temperature may depend on reaction time; the "optimum" reaction time may depend on cost, and so on. More particularly, suitable activation temperatures can vary from about 20 to 110° C. and the pH can vary from about 3 to 8 The reaction time can vary from 10 minutes to 24 hours or more, typically 1 to 4 hours for alpha-amylase.

The term "single phase", as used herein, means a mixture which has no visible free water, whereas a "slurry" consists of two phases, i.e. a water phase and a starch phase. Suitable total water content is from about 15 to 40% by weight of the total mixture.

A particularly useful converted starch material made in accordance with the above described single phase, enzyme conversion process is a maltodextrin having a reducing sugar content of between about 5 and 19 dextrose equivalents and a polymodal molecular weight distribution having one peak between about 630 and 1600 daltons and at least one other peak between about 1600 and 2,500,000 daltons. The maltodextrin product will have a solids content of at least 55% by weight and more particularly from about 60 to 80% by weight. Further descripton of the single phase, enzyme conversion process and the materials produced by such method can be found in the aforesaid '845 and 395 patents and the Ser. No. 08/643,719 pending application, all of which are hereby incorporated by reference The starches used in this invention may also be modified or derivatized by etherification or esterfication. Particularly useful modifications of starch are the hydroxyalkyl starches prepared by the etherification with alkylene oxides such as those containing 2 to 6, preferably 2 to 4 carbon atoms and especially ethylene and propylene oxide. Modifications of this type are generally made to provide a DS (degree of substitution) of from about 0 to 1 and preferably from about 0 to 0.5. Suitable ester substituent groups include succinate, octenylsuccinate, acetate, propionate, butyrate, hexanoate and benzoate groups.

A further embodiment of this invention is a blend of the starch with one or more synthetic polymers. Examples of synthetic polymers which may be used include: polyvinyl formamide, polyvinylpyrrolidone, polyvinyl acetate, polyvinyl alcohol, polyvinylpyrrolidone/vinyl acetate copolymers, polyvinylmethacrylate/methyl acrylate copolymers, acrylate copolymers, acrylate/potyvinylpyrrolidone copolymers, acrylate/vinyl acetate copolymers sodium polyacrylate, sodium polymethacrylate, octylacrylamide/acrylate/butylaminomethyl methacrylate copolymers, polyacryamide, sodium polystyrene sulfonate and styrene/acryate copolymers. Preferred synthetic polymers are polyformamide and polyvinylpyrrolidone and copolymers thereof. The proportion of starch to synthetic polymers in the blend can vary from about 100:0 to 25:75 percent by weight.

The starch or starch/synthetic polymer blend may be used in an amount of from about 5 to 80% and preferably from about 15 to 65% by weight, based on the total weight of the liquid formulation. The polymers are dissolved in a solvent such as water, ethanol or isopropanol and the solvent generally comprises from about 20 to 95% by weight of the composition.

Additive components may optionally be added to the formulation of this invention, if desired, and such additives include U.V. absorbers, plastsicizers, pigments, water swelling clay minerals, activators, vitamins and antiphogistics, fillers, surfactants, tack modifiers, skin modifiers, humectants and α- and β-hydroxy adds. Pigments which may be used include both organic and inorganic pigments such as titanium dioxide, silica and cellulose powders. A plasticizer can be added to the keratotic plug formulation and this can help in controlling the strength of the film when it is peeled from the skin and also improve the flexibility of a rigid polymer film. Examples of plasticizer components used in these compositions include; glycerin, propylene glycol, dipropylene glycol and butylene glycol.

The skin cleaning tape of this invention is prepared by applying the water-soluble starch adhesive formulation to a suitable backing strip or substrate. The backing substrate may be a non-woven or woven strip or sheet such as cotton, rayon and nylon cloth, knits, nets or apertured films and any other conventional backing material such as used in adhesive tapes, packs and poultice.

The starch formulation is applied to the backing substrate on one side by conventional methods and one technique involves applying the formulation to the flexible backing or tape by coating it in the form of a solution in a suitable vehicle such as water or organic solvent and evaporating the vehicle to provide a dried remoistenable adhesive film. The tape or coated substrate is applied to the skin area to be cleaned, usually facial areas such as nose, forehead, chin or cheeks, which is first washed or wetted with water, normal soap or face wash. The tape or backing material is applied to the wet surface so that the adhesive film is rewet and flows into the pores and attaches onto the keratotic plugs. The tape and film is allowed to dry, usually above 5 to 20 minutes, and then it, along with the dried adhesive film, is pulled off and removed from the skin. This mechanical action of removing the tape and adhesive causes the attached keratotic plugs as well as other attached dirt and debris to be pulled and removed from the pores.

Another technique of applying the starch formulation involves transfer coating in which the starch adhesive formulation is applied to a flexible release film. The coated film is then brought in contact with a backing substrate, the whole system dried and the solvent removed. The backing substrate is then removed leaving the dried film which is then applied to the skin area to be cleaned.

The following examples further illustrate the embodiments of this invention. In these examples, all parts and percentages are given by weight and all temperatures in degrees Celsius unless otherwise noted

EXAMPLE 1

A converted starch based adhesive composition was prepared using an α-amylase treated 35 WF waxy corn starch modified with 9% propylene oxide and converted to 10 DE. The starch was prepared using the single phase, high solids enzyme conversion process described above and further described in the aforementioned U.S. Pat. Nos. 5,688,845 and 5,795,397 and application Ser. No. 08/643,719. The starch was formulated into a composition which also contained glycerin and titanium dioxide and had the following formulation:

| Ingredients | Parts by Weight |
| --- | --- |
| Waxy corn (with propylene oxide)(10 DE) | 55 |
| Glycerin | 1 |
| Titanium dioxide | 3 |
| Deionized water | qs to 100 |

A nonwoven synthetic fiber was chosen as the backing for this system. In order to apply the composition to the backing, the formulation was coated onto a polyester film. The coating thickness on the polyester was 10 mil and this was controlled using a Bird Applicator. The nonwoven synthetic fiber was then laid on top of this coating and the whole system allowed to dry. Once the formulation was dried, the nonwoven was removed from the polyester and the coating had transferred from the polyester to the nonwoven. The film was white and very smooth and had no tack.

The dried film was then applied to the nose area of a human test model. The model first washed his face with soap and water and then applied this dried adhesive film to the wet tip of the nose. The adhesive film rewet and adhered to the skin. After drying for about 15 minutes, the pore cleansing strip was peeled from the nose. Keratotic plugs, dirt and other debris were quite visible on the pore cleansing tape after it was removed.

EXAMPLE 2

A converted starch base adhesive composition was prepared using a 50 WF waxy corn starch modified with 5% octenylsuccinic anhydride. The composition was diluted to 30% solids in water and had the following formulation:

| Ingredients | Parts by Weight |
| --- | --- |
| 50 WF waxy corn (with octenylsuccinic anhydride) | 25 |
| Glycerin | 1 |
| Deionized water | qs to 100 |

The formulation was applied to a nonwoven backing as in Example 1. The dried film was clear and had no tack. After application and removal, the tape again showed keratotic plugs, dirt and other debris.

EXAMPLE 3

A converted starch based adhesive was prepared as in Example 1 using an α-amylase treated 35 WF waxy corn starch modified with 9% propylene oxide and converted to 10 DE. This starch product was blended with a synthetic polymer, polyvinyl formamide, and formulated into the following composition:

| Ingredients | Parts by Weight |
| --- | --- |
| Waxy corn (with propylene oxide) (10DE) | 25 |
| Polyvinyl formamide | 25 |
| Glycerin | 1 |
| Titanium dioxide | 3 |
| Deionized water | qs to 100 |

The formulation was applied to the nonwoven backing as in Example 1. The film was white and very smooth and did not have tack. After application and removal, the tape again showed keratotic plugs, dirt and other debris.

What is claimed is:

1. A skin cleaning product comprising a substrate backing material with a starch based remoistenable adhesive composition applied to one surface of the substrate, the starch composition having about 0 to 70% by weight of amylose content, said starch having been converted to a degree of degradation in the range of from about 30 WF to 20 DE.

2. The skin cleaning product of claim 1 wherein the starch has from about 0 to 55% by weight of amylose content.

3. The skin cleaning product of claim 2 wherein the starch is modified with alkylene oxide having 2 to 6 carbon atoms to a DS of from about 0 to 1.

4. The skin cleaning product of claim 2 wherein the starch has been converted to a degree of degradation in the range of from about 70 WF to 10 DE.

5. The skin cleaning product of claim 1 wherein the starch has from about 0 to 30% by weight of amylose content.

6. The skin cleaning product of claim 5 wherein the starch is modified with alkylene oxide having 2 to 6 carbon atoms to a DS of from about 0 to 1.

7. The skin cleaning product of claim 6 wherein the starch has been converted to a degree of degradation in the range of from about 70 WF to 10 DE.

8. The skin cleaning product of claim 7 wherein the starch is waxy maize and the alkylene oxide is propylene oxide.

9. The skin cleaning product of claim 1 wherein the adhesive composition comprises a blend of the starch and a synthetic polymer in amounts of from about 100:0 to 25:75 percent by weight of starch to synthetic polymer.

10. The skin cleaning product of claim 9 wherein the synthetic polymer is polyvinyl formamide.

11. The skin cleaning product of claim 1 wherein the converted starch is a maltodextrin having a reducing sugar content of between about 5 and 19 dextrose equivalents and a polymodal molecular weight distribution having one peak between about 630 and 1600 daltons and at least one other peak between about 1600 and 2,500,000 daltons.

12. The skin cleaning product of claim 11 wherein the starch has from about 0 to 55% by weight amylose content.

13. The skin cleaning product of claim 11 wherein the starch has from about 0 to 30% by weight of amylose content and is modified with alkylene oxide having 2 to 6 carbon atoms to a DS of from about 0 to 1.

14. The skin cleaning product of claim 1 wherein the starch is prepared by a single phase, enzyme conversion process comprising the steps of:
 (a) adding, to a modified or unmodified, pregelatinized or ungelatinized starch, water and a starch-hydrolyzing enzyme in an amount sufficient to produce a single phase powdered mixture without a visible free water phase;
 (b) activating the enzyme by heating the powdered mixture to about the optimum temperature for the enzyme while maintaining a substantially constant moisture content in the mixture; and
 (c) allowing the enzyme to hydrolyze the starch.

15. The skin cleaning product of claim 14 wherein the starch has from about 0 to 55% by weight amylose content.

16. The skin cleaning product of claim 14 wherein the starch has from 0 to about to 30% by weight of amylose content, is modified with alkylene oxide having 2 to 6 carbon atoms to a DS of from about 0 to 1 and has been converted to a degree of degradation in the range of from about 70 WF to 10 DE.

17. The method of removing keratotic plugs and other dirt from skin surfaces which comprise applying a starch based adhesive composition which is attached to a substrate backing material to a wet skin surface, allowing the wetted starch composition to dry and removing the dried starch composition and backing material from the skin along with attached keratotic plugs and other dirt, wherein the starch composition has from about 0 to 70% by weight of amylose content, said starch having been converted to a degree of degradation in the range of from about 30 WF to 20 DE.

18. The method of claim 17 wherein the starch is modified with alkylene oxide having 2 to 6 carbon atoms to a DS of from about 0 to 1.

19. The method of claim 18 wherein the starch is modified with alkylene oxide containing 2 to 6 carbon atoms to a DS of from about 0 to 1.

20. The method of claim 19 wherein the starch has from about 0 to 30% by weight of amylose content.

21. The method of claim 20 wherein the starch is modified with alkylene oxide having 2 to 6 carbon atoms to a DS of about 0 to 1.

22. The method of claim 21 wherein the starch has been converted to a degree of degradation in the range of from about 70 WF to 10 DE.

23. The method of claim 22 wherein the starch is waxy maize and the alkylene oxide is propylene oxide.

24. The method of claim 17 wherein the starch is prepared by a single phase, enzyme conversion process comprising the steps of:

(a) adding, to a modified or unmodified, non-cold water soluble starch, water and a starch-hydrolyzing enzyme in an amount sufficient to produce a single-phase powdered mixture without a visible free water phase;

(b) activating the enzyme by heating the powdered mixture to about the optimum temperature for the enzyme while maintaining a substantially constant moisture content in the mixture; and (c) allowing the enzyme to hydrolyze the starch.

25. The method of claim 24 wherein the starch has from about 0 to 30% by weight of amylose content, is modified with alkylene oxide having 2 to 6 carbon atoms to a DS of from about 0 to 1 and has been converted to a degree of degradation in the range of from about 70 WF to 10 DE.

* * * * *